(12) United States Patent
Hill

(10) Patent No.: US 10,031,095 B2
(45) Date of Patent: Jul. 24, 2018

(54) METHOD FOR THE QUANTITATIVE ANALYSIS OF THE COMPOSITION OF A GAS MIXTURE AND ASSOCIATED MEASURING DEVICE

(71) Applicant: AREVA GMBH, Erlagen (DE)

(72) Inventor: Axel Hill, Stockstadt (DE)

(73) Assignee: AREVA GmbH, Erlangen (DE)

( * ) Notice: Subject to any disclaimer, the term of this patent is extended or adjusted under 35 U.S.C. 154(b) by 98 days.

(21) Appl. No.: 15/024,613

(22) PCT Filed: Sep. 24, 2014

(86) PCT No.: PCT/EP2014/070408
§ 371 (c)(1),
(2) Date: Mar. 24, 2016

(87) PCT Pub. No.: WO2015/044228
PCT Pub. Date: Apr. 2, 2015

(65) Prior Publication Data
US 2016/0238546 A1    Aug. 18, 2016

(30) Foreign Application Priority Data
Sep. 25, 2013   (DE) .......................... 10 2013 219 294

(51) Int. Cl.
*G01N 25/18* (2006.01)
*G01N 27/16* (2006.01)
*G01N 33/00* (2006.01)

(52) U.S. Cl.
CPC .............. *G01N 25/18* (2013.01); *G01N 27/16* (2013.01); *G01N 33/005* (2013.01)

(58) Field of Classification Search
CPC ....... G01N 25/18; G01N 27/16; G01N 33/005
See application file for complete search history.

(56) References Cited

U.S. PATENT DOCUMENTS 4,804,632 A    2/1989  Schuck et al.
5,297,419 A *  3/1994  Richardson ............ G01N 27/18
                                                          422/83

(Continued)

FOREIGN PATENT DOCUMENTS

CH    318487 A    1/1957
DE    3635513 A1  7/1987

(Continued)

*Primary Examiner* — Francis Gray
(74) *Attorney, Agent, or Firm* — Laurence A. Greenberg; Werner H. Stemer; Ralph E. Locher

(57) ABSTRACT

A method for the quantitative analysis of the composition of a gas mixture is specifically suited for the analysis of the atmosphere of a containment in a nuclear installation. Even under difficult conditions, this method enables the simple, reliable and as direct as possible determination of physical parameters, thereby permitting the characteristic definition of the ignition field and the combustion behavior of the gas mixture. A measuring device is provided with a thermal conductivity detector with a first measuring bridge, a thermal tonality detector with a second measuring bridge, and a common evaluation unit. With reference to bridge voltages present on the two measuring bridges, the hydrogen content and the oxygen content are simultaneously determined in the evaluation unit.

12 Claims, 2 Drawing Sheets

(56) References Cited

U.S. PATENT DOCUMENTS

| | | | |
|---|---|---|---|
| 2002/0076358 A1* | 6/2002 | Eckardt | G21C 9/06 |
| | | | 422/105 |
| 2008/0175345 A1* | 7/2008 | Hill | G01N 1/22 |
| | | | 376/256 |
| 2009/0035184 A1 | 2/2009 | Koda et al. | |
| 2016/0334376 A1* | 11/2016 | Gellert | G01N 30/62 |
| 2016/0341681 A1* | 11/2016 | Gellert | G01N 25/18 |

FOREIGN PATENT DOCUMENTS

| | | |
|---|---|---|
| DE | 3808305 A1 | 9/1989 |
| DE | 4112500 A1 | 10/1992 |
| DE | 102004060103 A1 | 12/2005 |
| DE | 102006033160 A1 | 1/2008 |
| DE | 102006059566 A1 | 6/2008 |
| JP | S5770435 A | 4/1982 |

* cited by examiner

METHOD FOR THE QUANTITATIVE ANALYSIS OF THE COMPOSITION OF A GAS MIXTURE AND ASSOCIATED MEASURING DEVICE

BACKGROUND OF THE INVENTION

Field of the Invention

The invention relates to a method for the quantitative analysis of the composition of a gas mixture, specifically the atmosphere of a containment of a nuclear installation. The invention also relates to an appropriate device for the execution of the method.

In nuclear installations with embedded nuclear fuel (e.g. nuclear power plants, processing plants and intermediate stores), in the event of incidents or accident situations, and depending upon the incident concerned and any countermeasures implemented, the potentially significant release of hydrogen must be anticipated. Due to an uncontrolled reaction with the oxygen present, this may result in combustion or even explosion, which will jeopardize the shell or containment.

Specifically in the event of comparatively severe incident situations, involving a potential core meltdown, hydrogen may be released within the containment in particularly high concentrations (e.g. 30% by volume) such that, in the presence of severe losses of leak-tightness in the containment shell, significant releases of hydrogen into the surrounding reactor building may also occur, as in the case of the Fukushima incident.

For the monitoring of existing protective measures for the maintenance of containment integrity (e.g. the action of catalytic recombiners), and prior to the deployment of "Severe Accident" measures (e.g. inert-gas blanketing and/or containment venting), knowledge is required of the relevant parameters for the combustibility of the containment atmosphere and the adjoining structural elements.

Specifically in inert-gas-blanketed containments (generally boiling water reactor containments), in addition to the hydrogen concentration, the maintenance of inserting and, accordingly, the simultaneous knowledge of movements in the oxygen concentration are significant to the appraisal of status and the targeted deployment of any measures required.

In principle, the early detection of the release of $H_2$ into the containment atmosphere is important for the appraisal of the accident profile and the planning of measures to be implemented. Accordingly, in the lower measuring range (up to the lower limit of inflammability), a higher accuracy of measurement is required than in the wider accident range (>10% by volume).

For these reasons, $H_2$ measurement is of safety-related significance, and is customarily executed in a redundant arrangement (i.e. single failure-proof).

For the measurement of $H_2$, previous measuring systems for the appraisal of the containment atmosphere or the progress of an accident require an elaborate sampling system with building isolation valves, together with an elaborate gas conditioning system for the condensation of water vapor and condensate drainage. For the measurement of $H_2$ and $O_2$ concentrations, two separate sensors, each with a dedicated functionality and corresponding electronic units for data processing, are required.

The routing of relatively large sample streams outside the containment, and their associated radioactivity, complicates the radiological qualification of sensors and their electronics, or renders their qualification for this application entirely unfeasible.

Moreover, these systems generate a high demand for electrical energy and/or require cooling water for the condensation of water vapor. However, specifically in the event of a postulated "station blackout", the supply of energy is problematic, or cannot be guaranteed.

It is particularly disadvantageous that, as a result of the condensation of water vapor, the true concentration of $H_2$ or $O_2$ must be back-calculated, such that only indirect determination is possible. Consequently, direct measurement is no longer involved. For the determination/calculation of the actual prevailing concentration by this methodology, further pressure and temperature measurements are required.

BRIEF SUMMARY OF THE INVENTION

The object of the present invention is the proposal of a method for the quantitative analysis of the composition of a gas mixture which avoids the above-mentioned disadvantages. Specifically, even under difficult conditions of the type prevailing in the event of a serious accident in a nuclear plant, this will enable the simple, reliable and as direct as possible determination of physical parameters, thereby permitting the characteristic definition of the ignition field and the combustion behavior of a gas mixture.

An appropriate device for the execution of the method is also proposed.

In respect of the method, the object according to the invention is fulfilled by the claimed method. In respect of the device, the object is fulfilled by the characteristics of the device claims.

The concept according to the invention differs from the existing prior art, in that it incorporates two methods of measurement based upon a resistance measurement in a Wheatstone bridge circuit, thereby enabling a redundant and diverse $H_2$ measurement, and also permitting a simultaneous measurement/balancing of the $O_2$ content.

One measuring bridge operates by the catalytic thermal tonality principle (TT detector), while the other measuring bridge operates by the thermal conductivity principle (TC detector). Signals from the thermal conductivity detector and the thermal tonality detector are routed to an electronic evaluation system for amplification and evaluation. One electronic system can process multiple sensors.

Both radiologically insensitive measuring chambers are preferably accommodated in a pressure- and temperature-resistant sensor housing, and are combined in an earthquake-resistant arrangement. The measuring chambers are connected to the containment atmosphere by a membrane, which may consist of a sintered metal. The combustible gases to be measured—hydrogen (alternatively carbon monoxide) and oxygen—are predominantly conveyed into the measuring cells by diffusion.

In addition, a temperature sensor is located at the site of measurement, employing the principle of resistance temperature measurement or thermal voltage measurement and used, for example, for the determination of vapor content, where saturated steam conditions are assumed.

The measurement of hydrogen concentration is preferably carried out in a diverse and redundant manner by the TC detector and the TT detector.

In the lower measuring range, up to the lower limit of inflammability, measurement is executed by the TT method, with the comparatively high accuracy of measurement required for incipient accidents (e.g. ±0.25% by volume).

At an oxygen content of the atmosphere below the stoichiometric composition of a $H_2/O_2$ mixture, measured values from the Wheatstone bridge circuit of the TT detector can be evaluated using a calibration curve for oxygen measurement. The $O_2$ concentration can thus be measured directly.

If a comparison reveals that the signals from the two measuring bridges are the same (in consideration of accuracy of measurement/tolerance), the $O_2$ concentration can be advantageously and indirectly determined by the measurement of the total thermal conductivity of the measuring gas, using the TC detector. To this end, plausible assumptions for the proportions of individual conductivities in the atmospheric composition in the containment are applied. As the initial air concentration is known, the $N_2$ concentration can be determined from the $H_2$ measurement, and the vapor concentration can be defined. The vapor concentration can be determined from the temperature measurement, on the assumption of saturated steam conditions. As a result, the error in the determination of $O_2$ is essentially dependent upon the error in $H_2$ measurement, and will be correspondingly smaller, the higher the accuracy of measurement of the $H_2$ content.

Key advantages of the concept according to the invention in comparison with the prior art may be summarized as follows:
Redundant and diverse hydrogen measurement in a single sensor head
Combined measurement in the $H_2$ combustion range (0-10% by volume) and in the wider measuring range (up to 100% by volume)
No oxygen required for $H_2$ measurement (particularly important for inert-gas-blanketed containments)
High accuracy in the range of the lower inflammability limit (at 4% by volume e.g. ±0.25% by volume)
Simultaneous measurement and/or balancing of $O_2$ concentration
Consequent facility for the appraisal of the ignition field and combustion behavior (combustion, explosion)
Direct $H_2/O_2$ measurement in inert-gas-blanketed containments with an $O_2$ concentration <5% by volume and an excess of $H_2$
In-situ measurement
No diversion of radioactivity outside the containment required
No containment isolation valves required
No conditioning of measuring gas required
High radiological resistance, as no employment of organic elements is required
No vulnerable electronics exposed to a "harsh environment" (containment)
Low power consumption (<500 W), which can be supplied by an independent battery unit in the event of a "station blackout"
Lower probability of failure
Faster measuring cycles (on-line measurement)
Smaller footprint
Less complex metrology
Lower investment costs
Straightforward retrofitting
Simple calibration

BRIEF DESCRIPTION OF THE SEVERAL VIEWS OF THE DRAWING

One exemplary embodiment of the invention is described in greater detail hereinafter, with reference to the drawings. These show a highly-simplified and schematic representation of the following.

DESCRIPTION OF THE INVENTION

Figure 1:
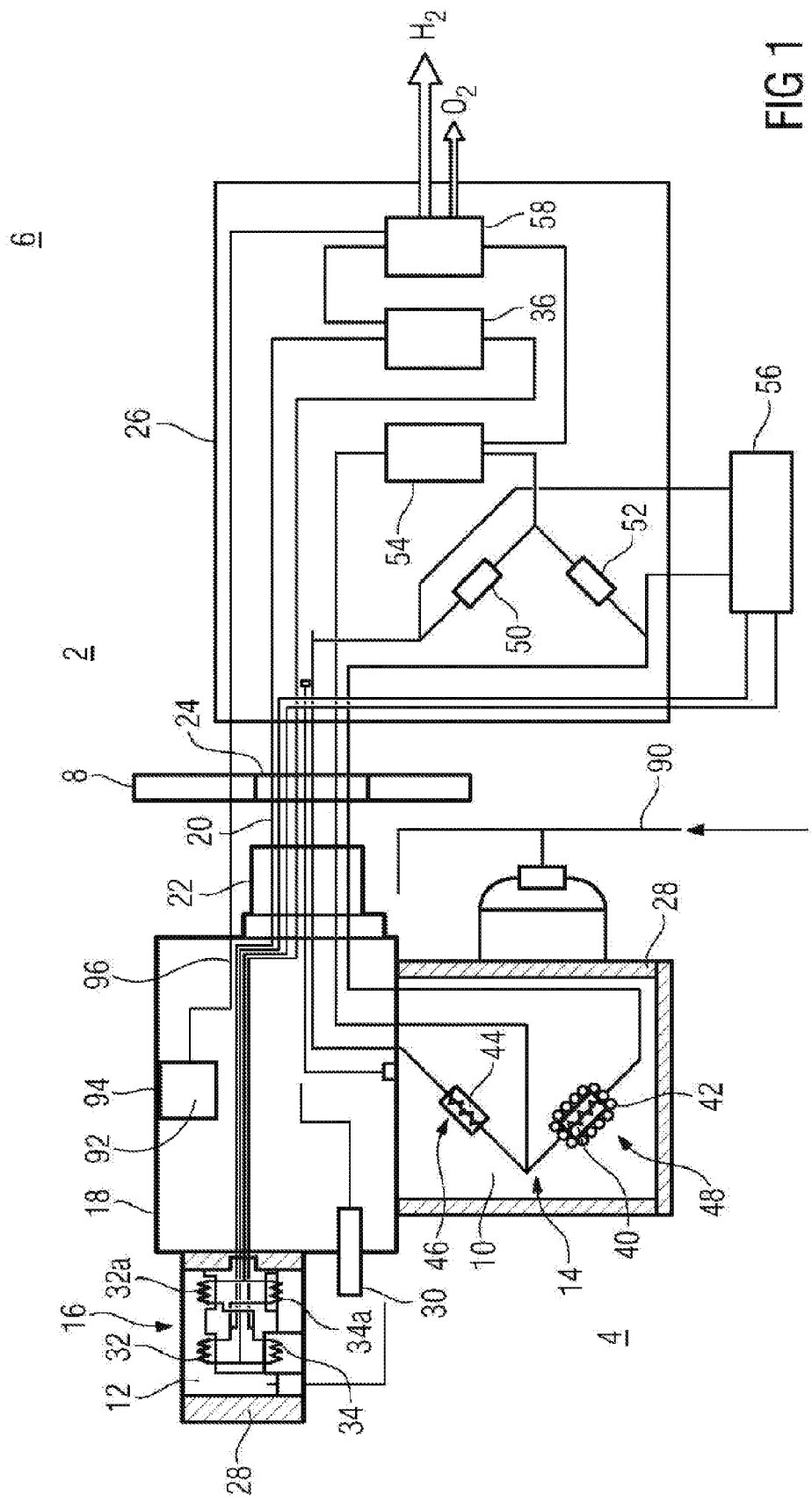
FIG. 1 a measuring system for the measurement of the concentration of the gas constituents of a gas mixture, in this case hydrogen and oxygen, in the containment atmosphere of a nuclear power plant, FIG. 2 a schematic circuit diagram of a particularly advantageous form of embodiment of a resistance bridge circuit for use in the measuring system according to FIG. 1, and FIG. 3 a diagram of calibration curves for a thermal tonality sensor in the measuring system according to FIG. 1.

The measuring device 2, a schematic overview of which is represented in FIG. 1, is primarily designed for the simultaneous determination of the content of hydrogen ($H_2$) and oxygen ($O_2$) in a measuring gas, specifically in the atmosphere of a safety enclosure of a nuclear power plant 6, also described as the containment 4. The containment shell itself, also described as the safety containment 8, is only partially represented here.

To this end, the measuring device 2 comprises two measuring chambers 10, 12, arranged in immediate spatial proximity to each other within the containment 4. This means that the clearance between the two measuring chambers 10, 12, in relation to the expansion of the containment 4, is sufficiently small, specifically less than 10 cm, such that reference can be made to a localized measurement at a spatial measuring point.

One of the measuring chambers, namely measuring chamber 10, forms a sensor head of a reaction heat detector, or catalytic thermal tonality detector, abbreviated to TT detector 14 or TTD, which operates by the principle of catalytic combustion or recombination. The other measuring chamber 12 forms a sensor head of a thermal conductivity detector, abbreviated to TC detector 16 or TCD.

In the exemplary embodiment, the two measuring chambers 10, 12 are mounted on a common electrical connection chamber 18, from which electrical connection lines 20 (signal lines and power lines) are routed via a failure-resistant connector 22 and a pressure-tight cable gland 24 in the safety containment 8 to an electronic evaluation unit 26 with an integrated or external power supply, arranged outside the containment 4. The connection lines 20 routed through the containment 4 may be configured, for example, as mineral-insulated cables. Distribution is expediently selected such that only the requisite and relatively radiation-resistant and robust electrical measuring cells for the execution of the measuring method are arranged in the measuring chambers 10, 12 within the containment 4, while the more sensitive components of the electronic evaluation system are located outside the containment 4.

The radiologically insensitive measuring cells in the two measuring chambers 10, 12 are each located in a pressure- and temperature-resistant housing and are combined in an earthquake-resistant arrangement. The measuring chambers 10, 12 are each fluidly connected to the containment atmosphere by a membrane 28, which may consist of a sintered metal. The gases to be measured are predominantly conveyed into the measuring chambers 10, 12 by diffusion.

In the immediate spatial vicinity of the TT detector 14 and the TC detector 16, a radiologically robust temperature sensor 30 which is also exposed to the stream of measuring gas is also arranged inside the containment 4, the connection lines of which are also routed via the connection chamber 18 and the cable gland 24 in the safety containment 8 to the electronic evaluation unit 26. The temperature sensor 30 is formed, for example, by a thermoelement.

In an unrepresented modification, the TT detector 14, the TC detector 16 and, where applicable, the temperature sensor 30 may be integrated in a common measuring chamber.

The TC detector 16 typically comprises a metal block with at least two identically constructed measuring cells 32, 34. One of the measuring cells 32 receives a stream of the gas to be analyzed, the sample gas or measuring gas, while the other measuring cell 34 is permanently isolated from the surrounding measuring gas, and instead receives a stream of a pure gas of preferably known and constant composition. This measuring cell 34, which is isolated from the volume of measuring gas, is used for comparative measurement.

Each of the measuring cells 32, 34 also accommodates a heating wire (also described as a filament), for example of platinum, tungsten, nickel or alloys thereof, which is heated to a higher temperature than the surrounding detector block. A continuous flow of heat is therefore delivered by the heating wires through the surrounding gas streams to the detector block, which is dependent upon the thermal conductivity (and consequently the composition) of the gases. Variations in the composition of the measuring gas therefore result in temperature variations in the measuring cell 32, and a consequent variation in the electrical resistance of the heating wires. The principle of measurement is thus based upon the continuous measurement of the difference in the thermal conductivity of the sample gas stream, in relation to a reference gas stream.

As the measuring and reference cells 32, 34 are combined in a Wheatstone bridge circuit, temperature differences between the heating wires can be measured as a voltage difference, and recorded accordingly. In this arrangement, the heating wires of the two measuring cells 32, 34 form two electrical resistances which are arranged in the manner of a voltage divider, and balanced with a parallel-connected voltage divider via an intervening bridging path. The detector signal thus measured is proportional to a first approximation of the sample concentration, in this case e.g. the concentration of $H_2$ in the measuring gas.

In the variant represented in FIG. 1, a total of four measuring cells 32, 32a, 34, 34a are arranged in the measuring chamber 12, which interact in pairs as measuring and reference cells. In each of the two voltage divider strings, which are supplied through one of the diagonals with the service voltage and, in the other diagonal (via the bridging path), are mutually balanced via a voltage measuring unit, one measuring cell and one reference cell are therefore arranged respectively. The voltage measuring unit is integrated in the form of a thermal conductivity evaluation module 36 in the evaluation unit 26 which is arranged outside the containment 4.

In an alternative unrepresented variant with a total of two measuring cells 32, 34, the voltage divider arranged opposite the voltage divider formed by the measuring and reference cells may be formed of two fixed resistors, which may be specifically located in the evaluation unit 36.

The TT detector 14 also operates in a known manner:

Through the membrane 28 of the measuring chamber 10, specifically configured as a porous sintered metal disk, the measuring gas enters the measuring chamber 10. The latter accommodates two heating elements in the form of resistance wires which, by the application of a heating voltage, are heated to a working temperature of the order of 500 to 600° C. One of the heating elements, the pellistor 40, is surface-coated with a catalyst 42, such that any hydrogen ($H_2$) present, in the simultaneous presence of oxygen ($O_2$), is catalytically combusted to form water vapor ($H_2O$) or recombined flamelessly. The resulting temperature increase leads to an increase in the electrical resistance of the heating wire of the pellistor 40. The second heating element, the compensator 44, is coated with a chemically inert layer and serves as a reference resistance for the pellistor 40. Environmental influences such as temperature and atmospheric humidity, which result in an alteration in the temperature of the heating elements, can be compensated in this way.

In the recombination reaction, the difference in the resistance values of the measuring cells 46, 48 formed by the pellistor 40 and the compensator 44, in a similar manner to the TC detector 16, is measured by means of a Wheatstone measuring bridge. In the variant represented in FIG. 1, the two fixed resistors 50, 52 in the second voltage divider string are accommodated in the external evaluation unit 26. Measurement of the bridging voltage proceeds in the thermal tonality evaluation module 54.

An independent current/voltage supply unit 56, which is specifically configured according to the principle of an uninterruptible power supply (UPS), assumes the supply of current/voltage to the bridge circuits and the evaluation modules.

Via a feed line 90, for testing and calibration purposes, a test gas of a well-defined and known composition may be introduced into the measuring chambers 10, 12.

The bridging voltages detected in the thermal conductivity evaluation module 36 and the thermal tonality evaluation module 56 may be processed, for example, directly in these modules and/or in a down-circuit measuring data processing module 58, in the manner described hereinafter.

Figure 2:
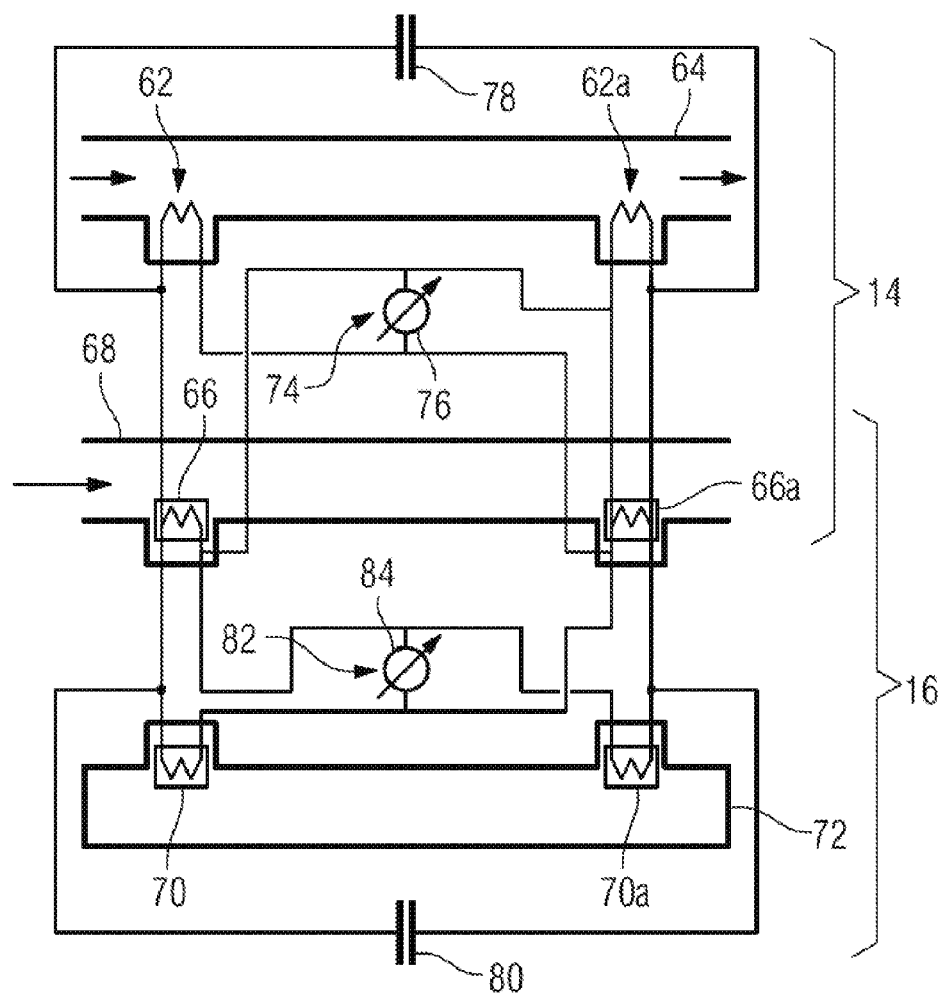

A particularly advantageous variant of a resistance bridge circuit, in which the TT detector 14 and the TC detector 16 are integrated in a common circuit with two measuring bridges, is schematically represented in FIG. 2.

The dual bridge circuit 60 comprises two similar and catalytically active measuring cells 62, 62a, which are surrounded or traversed by the measuring gas stream, as represented schematically by the flow channel 64. It also comprises two similar and catalytically inactive measuring cells 66, 66a, which are also surrounded or traversed by the measuring gas stream, as represented schematically by the flow channel 68. Alternatively, the measuring cells may also be arranged in a common flow channel for the measuring gas, provided that, by means of an appropriately selected minimum clearance, any thermal cross-talk between the active and inactive measuring cells can be prevented. Finally, there are two further similar and catalytically inactive measuring cells 70, 70a, which are isolated from the measuring gas, as represented schematically by the arrangement thereof in a comparative volume 72, which is sealed from the environment and is specifically filled with a reference gas.

Wiring is selected such that the catalytically inactive measuring cells 66, 66a surrounded by the measuring gas in the center are available as reference cells, both for the catalytically active measuring cells 62, 62a surrounded by the measuring gas above, and for the catalytically inactive measuring cells 70, 70a isolated from the measuring gas below. Accordingly, on the one hand, the catalytically inactive measuring cells 66, 66a surrounded by the measuring gas in the center, in combination with the catalytically active measuring cells 62, 62a surrounded by the measuring gas above, form a detector operating by the thermal tonality principle (TT detector 14) and, on the other hand, in combination with the catalytically inactive measuring cells 70, 70a which are isolated from the measuring gas below, form a detector operating by the thermal conductivity principle (TC detector 16). Evidently, the designations "above, below, in the center" are only provided in the interests of the clearer legibility of the drawing, and do not constitute any restriction on the actual spatial arrangement of the measuring cells.

In practice, each catalytically active measuring cell surrounded by the measuring gas (e.g. 62), with its diagonally-opposite catalytically inactive measuring cell surrounded by the measuring gas (e.g. 66a) forms a voltage divider of the TT detector 14, which is coupled to the other of the two voltage dividers by the bridging path 74. A voltage measuring device 76 for the measurement of the TT bridge voltage is connected in the bridging path 74. The supply of voltage to the bridge circuit is delivered by the voltage source 78.

For the mirror-image circuit of the TC detector 16 with the measuring cells 66, 66a and 70, 70a, the above-mentioned descriptions apply correspondingly. In this case, the voltage source 80 assumes the supply of voltage to the measuring bridge, and a voltage measuring device 84 for the measurement of the TC bridge voltage is connected in the bridging path 82.

A key advantage of this circuit in relation to other conceivable variants is that fewer cables need to be routed to the sensors.

As a result of the comparatively low sensitivity of the TC detector 16, this is preferably used in the present case for the measurement of the concentration of $H_2$ in the upper range of measurement >10% by volume to 30% by volume, up to 100% by volume (the "wider accident range").

The TC detector 16 can also be used for an approximate measurement of the $H_2$ concentration in the lower range of measurement <10% by volume, specifically for comparative measurement and a comparison with the TT detector 14 for the purposes of consistency.

Specifically a measurement of the $H_2$ concentration in the measuring gas can be executed using the TC detector 16, when only little or no oxygen is present in the measuring gas. This is possible, as the operation of the TC detector 16, as described above, is not dependent upon the presence of $O_2$ in the measuring gas. A situation of this type, with a lack of oxygen, is reliably detectable using the TT detector 14, as the catalytic recombination which normally proceeds on the latter is dependent upon a sufficient oxygen content in the measuring gas.

Finally, the $H_2$ concentration measured by the TC detector 16 is used as an input variable for the catalytically-supported determination of the $O_2$ concentration by an interaction with the TT detector 14, as further described below.

The TT detector 14 is preferably used for the measurement of the $H_2$ concentration in the lower range of measurement <10% by volume, in the presence of a sufficient, and preferably at least stoichiometric $O_2$ content, for the initiation and maintenance of the recombination reaction. Accordingly, even in the early stages of a severe accident, a rapid and secure detection of the release of $H_2$ and the monitoring of the corresponding concentration profile can be achieved.

As the efficiency of $H_2/O_2$ recombination, and consequently the bridge voltage measured by the TT detector 14 is dependent upon the content of both of the gas components in the measuring gas, it is also possible in principle to determine the $O_2$ concentration using the TT detector 14.

At sufficiently high $H_2$ concentrations, for example >10% by volume, this may be achieved directly, on the basis of empirical bridge voltage characteristics previously determined by test series and theoretically justified where applicable, as a function of the $H_2$ concentration on the one hand and the $O_2$ concentration on the other. In summary, the measurement of the $O_2$ concentration under the specified conditions of high $H_2$ concentration proceeds by the calibration of the measuring signal for the catalytic reaction on the TT detector 14.

Figure 3:
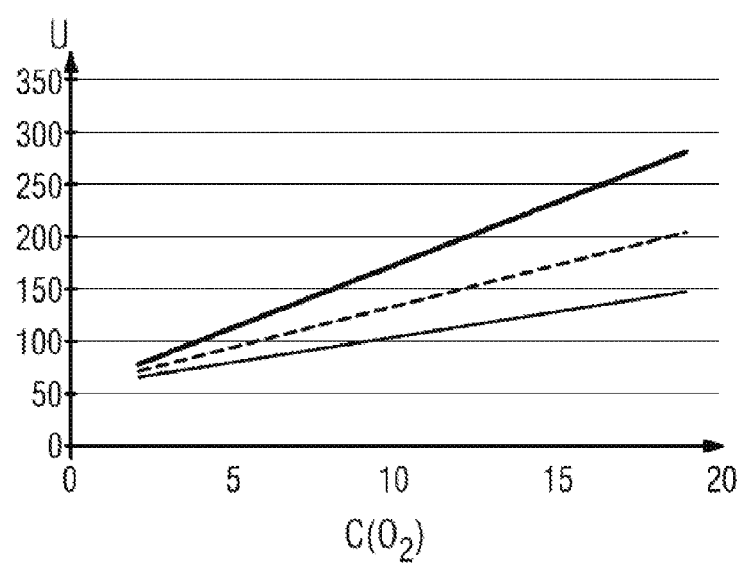

This is exemplified in FIG. 3: here, the bridge voltage U measured on the TT detector 14 in mV as a function of the $O_2$ concentration $C(O_2)$ in % by volume is plotted schematically for three different $H_2$ concentrations (10, 20 and 30% by volume) as a parameter for the set of curves. In the interval represented, the curve profile is approximately linear. At a known $H_2$ concentration, specifically given by the measured value from the TC detector 16, the measured bridge voltage permits the $O_2$ concentration to be clearly read from the set of curves (where applicable by interpolation).

Similar characteristics can be determined for the bridge voltage as a function of the $H_2$ concentration, with the $O_2$ concentration as the group parameter.

At low $H_2$ concentrations, for example <2.5% by volume, with a correspondingly reduced catalytic reaction, the determination of $O_2$ concentration proceeds indirectly and semi-analytically by the measurement of the total thermal conductivity of the measuring gas using the TC detector 16, and by the deduction of the individual conductivities and gas concentrations on the basis of additional assumptions—specifically by the determination of the vapor concentration by means of temperature measurement, assuming saturated steam conditions.

In this case, evaluation is based, for example, upon the following assumptions:

If it is assumed that the containment firstly contains air at an ambient temperature of 293 K, and then at the start of an accident hydrogen ($H_2$) and water vapor ($H_2O$) are predominantly released in the first instance, the assumption of conservation of mass in the containment gives the following relationships for the concentrations C and pressures p:

$$C(total)=C(air)+C(H_2)+C(H_2O)=1 \tag{1}$$

$$p(total)=p(air)+p(H_2)+p(H_2O) \tag{2}$$

The air initially present is essentially comprised of oxygen ($O_2$) and nitrogen ($N_2$), whereby the oxygen concentration in the containment changes as the accident proceeds, as a result of oxidation reactions, whereas the nitrogen is inert and is not involved in the reaction process. The proportion thereof in the air initially present is known to be approximately 79%:

$$C(N_2)=0.79C(air) \tag{3}$$

The total thermal conductivity of the measuring gas measured using the TC detector 16 can be superimposed, in an effective approximation, by the addition of the individual conductivities of the constituents $H_2$, $O_2$, $N_2$ and $H_2O$:

$$\lambda(total)=\lambda(H_2)C(H_2)+\lambda(O_2)C(O_2)+\lambda(N_2)C(N_2)+\lambda(H_2O)C(H_2O) \tag{4}$$

Here, $\lambda$ represents the specific thermal conductivities known from the literature.

Moreover, the individual concentrations can be expressed as follows by the partial pressures of the individual constituents:

$$C(H_2O)=p(H_2O)/p(total) \tag{5}$$

$$C(H_2)=p(H_2)/p(total) \tag{6}$$

$$C(H_2O)=p(H_2O)/p(total) \tag{7}$$

The partial pressure of air can be approximated using the ideal gas law p=k T as follows:

$$p(air)=1\ bar*T/293\ K \quad (8)$$

Here, T represents the temperature of the measuring gas, which is measured by the temperature sensor 30. The constant k has been standardized at an ambient pressure of 1 bar at an ambient temperature of 293 K (=20° C.).

On the further assumption of saturated steam conditions (an equilibrium of vapor pressure associated with an equilibrium of the liquid and vapor phase), the partial pressure of water vapor $H_2O$ can be derived from standard tables as a function of the measured temperature:

$$p(H_2O)=p_{steam}(T) \quad (9)$$

If the equations (1) to (3) and (5) to (9) are now incorporated into equation (4) for the deduction of the oxygen concentration, the resulting expression is only dependent upon the directly measurable variables λ(total), $C(H_2)$ and T, and upon parameters which are known from the literature λ($H_2$), λ($O_2$), λ($N_2$), λ($H_2O$), together with the likewise known saturation vapor pressure curves for water vapor $H_2O$:

$$C(O_2)=F(\lambda(total),C(H_2),T|\lambda(H_2),\lambda(O_2),\lambda(N_2),\lambda(H_2O)) \quad (10)$$

In this way, under the assumptions adopted $C(O_2)>C(H_2)$ and $C(H_2)\approx<2.5\%$ by volume, the oxygen concentration $C(O_2)$ can be determined from the measured value λ(total) on the TC detector 16, the measured value $C(H_2)$ on the TT detector 14, obtained by a similar calibration process to that described above, and the measured value for the temperature T of the measuring gas obtained from the temperature sensor 30.

A standard error calculation by Gaussian approximation, under the additional assumption that the major element of error originates from the measured $H_2$ concentration, gives the measurement error as follows (standard deviation):

$$\Delta C(O_2)\approx(\lambda(H_2)/\lambda(O_2))\Delta C(H_2)\approx 7\Delta C(H_2) \quad (11)$$

Accordingly, the value for the $O_2$ concentration thus determined is unavoidably impaired by a measurement error, which is approximately seven times greater than the measurement error for the $H_2$ concentration. Nevertheless, under the justifiable assumptions made for conditions in the early stages of a severe accident, this is a reasonable approximation.

The evaluations and calculations described above are appropriately automated in the measuring data evaluation module 58, which is equipped with the corresponding hardware and/or software for this purpose.

Preferably, a consistency comparison is executed on the measured values delivered by the two detectors 14 and 16, and an automatic selection of the most appropriate evaluation method under the circumstances proceeds on the basis of the above-mentioned criteria.

As may be inferred from the above description, in the range of low $H_2$ concentrations <10% by volume, the determination of the $O_2$ concentration proceeds by the catalytic thermal tonality method, or in approximation by the combination of thermal conductivity and catalytic thermal tonality, specifically in the range of measurement of high $O_2$ concentrations >15% by volume. This can specifically occur if the entire $H_2$ content of the atmosphere—in any event in the environment of the sensor head—is converted in the catalytic reaction.

In order to permit the reliable determination of the $O_2$ concentration under these conditions with relatively high accuracy, even where little or no hydrogen is present in the atmosphere, a zirconium dioxide measuring cell 92 is advantageously integrated into the sensor head, in addition to the TC/TT measuring cells. The reference gas required for measuring purposes (preferably air) is contained in a sensor head chamber which is hermetically sealed from the environment. A zirconium dioxide membrane 94 which is heated, for example, by an electric heating element, separates the reference gas from the containment atmosphere.

The functional method is as follows: with effect from a temperature of approximately 650° C., the following fundamental physical mechanisms occur in zirconium dioxide ($ZrO_2$):

$ZrO_2$ isolates oxygen ions, and becomes a solid body electrolyte for oxygen. By the application of a current source, surrounding oxygen can be transported through the $ZrO_2$.

As the $ZrO_2$, at the temperatures specified, acts as an electrolyte, a galvanic voltage ("Nernst voltage") can be measured, in the presence of an oxygen pressure differential at the boundary surfaces of the $ZrO_2$ element.

It is therefore possible, using the heated $ZrO_2$ measuring cell 92, to determine the oxygen content of the surrounding atmosphere relative to the reference gas by a potentiometric method. The corresponding measurement signal is routed via the additional signal line 96 of the evaluation unit 26 and is evaluated therein, thereby permitting the determination of the $O_2$ content in the measuring atmosphere.

Thus, in the specified range of low $H_2$ concentrations (<10% by volume), $ZrO_2$-based measurement is effective as a redundant measuring method, and high accuracies can be achieved over the full range of measurement for $O_2$ (customarily from 0 to 25% by volume).

At $H_2$ concentrations >10% by volume, at unfavorable $O_2$ concentrations, the heated $ZrO_2$ measuring method at the temperatures specified may result in the spontaneous reaction of the $H_2$ content (detonation gas reaction or ignition). In order to prevent this process, at higher $H_2$ contents in excess of 10% by volume, the $ZrO_2$-based measuring method is disconnected from the common electronic evaluation system and, specifically, the heating element for the heating of the $ZrO_2$ membrane 94 is deactivated. The measured values of the $H_2$ concentration required for this purpose are preferably delivered by thermal conductivity measurement. In the range of $H_2$ concentrations >10% by volume, the measurement of $O_2$ concentration then proceeds as described above, by the combination of TC/TT measurement.

Although the measuring device 2 has thus far been described with exclusive reference to the monitoring of the atmosphere in a containment of a nuclear power plant, it is clear that it is also suitable for use in other nuclear installations, including an intermediate storage facility or processing plant. Moreover, the application thereof in any industrial installation in which the release of hydrogen and oxygen might be anticipated, and in which there is a consequent risk of a gas detonation is also conceivable. The measuring principle can also ultimately be applied to other gases which can be catalytically recombined with each other.

LIST OF REFERENCE NUMBERS

2 Measuring device
4 Containment
6 Nuclear power plant
8 Safety containment 10 Measuring chamber
12 Measuring chamber
14 TT detector
16 TC detector
18 Connection chamber
20 Connection lines
22 Connector
24 Cable gland
26 Evaluation unit
28 Membrane
30 Temperature sensor
32, 32a Measuring cell
34, 34a Measuring cell
36 TC evaluation module
40 Pellistor
42 Catalyst
44 Compensator
46 Measuring cell
48 Measuring cell
50 Fixed resistor
52 Fixed resistor
54 TT evaluation module
56 Current/voltage supply unit
58 Measuring data evaluation module
60 Bridge circuit
62, 62a Measuring cell
64 Flow channel
66, 66a Measuring cell
68 Flow channel
70, 70a Measuring cell
72 Comparative volume
74 Bridging path
76 Voltage measuring device
78 Voltage source
80 Voltage source
82 Bridging path
84 Voltage measuring device
90 Feed line
92 Zirconium dioxide measuring cell
94 Zirconium dioxide membrane
96 Signal line

The invention claimed is:

1. A method for quantitative analysis of the composition of a gas mixture, the method comprising:
providing a measuring device with
a thermal conductivity detector having a first measuring bridge;
a reaction heat detector having a second measuring bridge; and
an evaluation unit;
using the evaluation unit for determining a hydrogen content and, at the same time, determining an oxygen content in the gas mixture based on respective bridge voltages present at the first and second measuring bridges.

2. The method according to claim 1, which comprises analyzing an atmosphere of a containment of a nuclear plant.

3. The method according to claim 1, which comprises determining two measured values for the hydrogen content in the evaluation unit in diversitary processes based on the bridge voltages present at the first and second measuring bridges.

4. The method according to claim 1, which comprises, in case of hydrogen concentrations of >10% by volume, determining the oxygen content directly from an empirically determined calibrating curve for the bridge voltage present on the measuring bridge of the reaction heat detector.

5. The method according to claim 1, which comprises, in case of hydrogen concentrations of <2.5% by volume, determining the oxygen concentration based on
a thermal conductivity of the gas mixture measured on the thermal conductivity detector;
a hydrogen concentration of the gas mixture determined by calibration on the reaction heat detector; and
a temperature of the gas mixture determined by way of a temperature sensor;
wherein a vapor pressure of water vapor present in the gas mixture is determined from the temperature, for the evaluation, assuming a saturation.

6. The method according to claim 1, which comprises, in case of hydrogen concentrations of <10% by volume, determining the oxygen content redundantly by measuring a galvanic voltage tapped at a heated zirconium dioxide measuring cell.

7. The method according to claim 6, which comprises switching off a heating of the zirconium dioxide measuring cell if the hydrogen concentration determined by one or both of the thermal conductivity detector or the reaction heat detector is >10% by volume.

8. A measuring device for quantitative analysis of a composition of a gas mixture, the measuring device comprising:
a thermal conductivity detector having a first measuring bridge;
a reaction heat detector having a second measuring bridge; and
a common evaluation unit connected to said thermal conductivity detector and to said reaction heat detector, said evaluation unit being configured for carrying out the method according to claim 1.

9. The measuring device according to claim 8, configured for analyzing an atmosphere of a containment of a nuclear plant.

10. The measuring device according to claim 8, wherein:
said second measuring bridge of said reaction heat detector is formed by two catalytically active measuring cells surrounded by the measuring gas together with two catalytically inactive cells surrounded by the measuring gas; and
said first measuring bridge of said thermal conductivity detector is formed by two catalytically inactive measuring cells isolated from the measuring gas together with said two catalytically inactive cells surrounded by the measuring gas.

11. The measuring device according to claim 8, comprising a heatable zirconium dioxide measuring cell for a diversitary redundant determination of an oxygen content in said evaluation unit, in case of hydrogen concentrations of <10% by volume.

12. A monitoring system for the atmosphere in a containment of a nuclear plant in case of severe hazardous incidents, the monitoring system comprising a measuring device according to claim 8.

* * * * *